(12) United States Patent
Longenecker

(10) Patent No.: US 11,622,538 B2
(45) Date of Patent: Apr. 11, 2023

(54) APPARATUS AND METHOD FOR CATCHING ANIMAL URINE

(71) Applicant: Julie Marie Longenecker, South Saint Paul, MN (US)

(72) Inventor: Julie Marie Longenecker, South Saint Paul, MN (US)

(*) Notice: Subject to any disclaimer, the term of this patent is extended or adjusted under 35 U.S.C. 154(b) by 138 days.

(21) Appl. No.: 17/249,036

(22) Filed: Feb. 18, 2021

(65) Prior Publication Data

US 2021/0307293 A1 Oct. 7, 2021

Related U.S. Application Data

(60) Provisional application No. 63/005,679, filed on Apr. 6, 2020.

(51) Int. Cl.
*A01K 23/00* (2006.01)
*A61F 13/64* (2006.01)

(52) U.S. Cl.
CPC .............. *A01K 23/00* (2013.01); *A61F 13/64* (2013.01)

(58) Field of Classification Search
CPC .................. A01K 23/00; A01K 13/006; A61F 2013/15186; A61F 13/64
USPC ..... 119/868, 850, 869, 858, 863; 128/107.1; D30/145
See application file for complete search history.

(56) References Cited

U.S. PATENT DOCUMENTS

| | | | |
|---|---|---|---|
| 3,738,330 A * | 6/1973 | Alofsin .................. | A01K 21/00 119/838 |
| 3,792,687 A | 2/1974 | Ehrman | |
| 4,577,591 A | 3/1986 | Wesseldine | |
| D383,259 S * | 9/1997 | Post .............................. | D24/124 |
| 5,954,015 A * | 9/1999 | Ohta ....................... | A01K 23/00 119/850 |
| 6,854,427 B2 | 2/2005 | Frink | |
| 7,464,668 B2 | 12/2008 | Brewington | |
| 7,581,514 B2 | 9/2009 | Bonfoey | |
| 8,302,565 B2 | 11/2012 | Williams | |
| 8,656,866 B2 | 2/2014 | Moharram | |
| 8,992,495 B1 | 3/2015 | Howell | |
| 9,713,316 B1 | 7/2017 | Muse, Jr. | |
| 10,238,090 B2 | 3/2019 | Zoltanski | |
| 10,506,797 B2 | 12/2019 | Hanes | |
| 2005/0061260 A1 | 3/2005 | Hall | |
| 2007/0012263 A1 | 1/2007 | Hammonds | |

(Continued)

OTHER PUBLICATIONS

Longenecker, J. (Apr. 14, 2019) Male dog belly band belly band wraps senior dogs potty. Retrieved Feb. 16, 2021, from https://www.etsy.com/listing/684971058/male-dog-belly-band-belly-band-wraps?ref=shop_home_feat_3.

*Primary Examiner* — Yvonne R Abbott-Lewis
(74) *Attorney, Agent, or Firm* — Dunlap Bennett & Ludwig, PLLC

(57) ABSTRACT

A band for attachment to a midsection of an animal is disclosed. The band includes a central portion, a first and second buckle strap, and a buckle. The first and second buckle straps are integral with the central portion and taper to a uniform width. The central portion has a width greater than the uniform width of the first and second buckle straps. The buckle includes a male buckle secured to a distal end of the first buckle strap and a female buckle secured to a distal end of the second buckle strap. The buckle is designed to latch over a back of the animal, and the protective liner is designed to cover an underside of the animal, in use.

15 Claims, 3 Drawing Sheets

(56) References Cited

U.S. PATENT DOCUMENTS

| | | |
|---|---|---|
| 2010/0319633 A1 | 12/2010 | Moncheski |
| 2011/0239957 A1 | 10/2011 | Washington |
| 2014/0102381 A1 | 4/2014 | Siano |
| 2017/0156295 A1* | 6/2017 | Zoltanski ............. A01K 13/006 |
| 2017/0231193 A1 | 8/2017 | Allman |
| 2019/0307104 A1 | 10/2019 | Dragon et al. |
| 2019/0380309 A1 | 12/2019 | Birchler |
| 2020/0253165 A1* | 8/2020 | Luciew .................. A61F 13/82 |

* cited by examiner

APPARATUS AND METHOD FOR CATCHING ANIMAL URINE

CROSS-REFERENCE TO RELATED APPLICATION

This application claims the benefit of priority of U.S. provisional application No. 63/005,679, filed Apr. 6, 2020, the contents of which are herein incorporated by reference.

BACKGROUND OF THE INVENTION

The present invention relates to catching animal (e.g., a pet) urine and, more particularly, to a slim-profile, fabric band with a buckle closure to catch animal urine.

There are many instances where animals, such as dogs, might urinate unexpectedly. Dogs who have been rescued are often fearful of loud noises and may urinate or bite when they hear loud noises. Dogs who are not yet potty trained urinate inside the house. Dogs may mark an owner's home, or the homes of family or friends, by urinating on furniture, and dogs who have bladder issues, like urine leakage, urinate as they walk. Bands placed around dogs' midsections, commonly referred to as "belly bands", are conventionally used to prevent urination from occurring, but many dogs can remove the belly bands when uncomfortable to wear and the closure to secure the band is a hook and fastener type, such as VELCRO™.

Furthermore, hook and loop fasteners make a loud ripping sound when they are pulled apart, and this sound scares many dogs. Hook and loop fasteners get dirty easily, as debris gets trapped in the hook and loop portions, and it ceases securely fastening over time. In conventional products, the band size covers a large area on a dog's back, and the dog can pull the hook and loop fastener closure open and remove the belly band. Dogs can remove the belly band by opening the hook and loop fastener closure, while opening of the closure is loud and can scare the dog. These conventional bands are bulky and uncomfortable to wear, which is likely why dogs want to remove them in the first place.

As can be seen, there is a need for slim-profile belly band with a buckle closure to catch dog urine.

SUMMARY OF THE INVENTION

In one aspect of the present invention, a band for attachment to a midsection of an animal comprises: a central portion comprising a protective liner and having a first central portion width; a first buckle strap integral with and disposed on a first side of the central portion, the first buckle strap tapering in width from a first buckle strap width, proximal the central portion, to a second buckle strap width smaller that is smaller than the first buckle strap width, with the first buckle strap width having a smaller width that the first central portion width; a second buckle strap integral with and disposed on a second side of the central portion opposite the first side, the first buckle strap tapering in width from a third buckle strap width, proximal the central portion, to a fourth buckle strap width smaller that is smaller than the third buckle strap width, with the third buckle strap width having a smaller width that the first central portion width; and a buckle comprising a male buckle secured to a distal end of the first buckle strap and a female buckle secured to a distal end of the second buckle strap, the buckle being configured to latch over a back of the animal, and the protective liner being configured to cover an underside of the animal.

In another aspect of the present invention, a method of covering a midsection of an animal comprises: providing a band comprising: a central portion comprising a protective liner and having a first central portion width; a first buckle strap integral with and disposed on a first side of the central portion, the first buckle strap tapering in width from a first buckle strap width, proximal the central portion, to a second buckle strap width smaller that is smaller than the first buckle strap width, with the first buckle strap width having a smaller width that the first central portion width; a second buckle strap integral with and disposed on a second side of the central portion opposite the first side, the first buckle strap tapering in width from a third buckle strap width, proximal the central portion, to a fourth buckle strap width smaller that is smaller than the third buckle strap width, with the third buckle strap width having a smaller width that the first central portion width; and a buckle comprising a male buckle secured to a distal end of the first buckle strap and a female buckle secured to a distal end of the second buckle strap, the buckle being configured to latch over a back of the animal, and the protective liner being configured to cover an underside of the animal. positioning the central portion such that the protective liner covers an underside of the pet; and latching the buckle over a back of the animal.

These and other features, aspects and advantages of the present invention will become better understood with reference to the following drawings, description, and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a band for attachment to a midsection of an dog/animal. The band includes a central portion comprising a protective liner and having a first central portion width. It also includes a first buckle strap and a second buckle strap. Each buckle strap is integral with and disposed on an opposing side of the central portion and tapers in width from a first buckle strap width proximal the central portion to a second buckle strap width smaller than the first buckle strap width. Further, the first buckle strap width and the second buckle strap width have a smaller width that the first central portion width. The band also includes a buckle that has a male buckle secured to a distal end of the first buckle strap and a female buckle secured to a distal end of the second buckle strap. The buckle (and band in general) is designed to latch over a back of the dog, and the protective liner is designed to cover an underside of the dog, in use. It should be understood that, while the present invention is largely described in the context of use with dogs, a person of ordinary skill in the art will appreciate that these teachings may be applied to bands for various other animals who may require some type of diaper.

Advantageously, embodiments of the present invention reduce the amount of material that lays on a dog's back, resulting in a more comfortable experience for the dog. Further, the reduction in material in the top-laying section and the use of a buckle rather than other methods of fastening (such as hook and loop fasteners) provides a major functional advantage over the prior art because embodiments of the present invention are much more difficult to remove by the pet. Thus, the dog is more comfortable, and the band reliably stays secured to the dog.

Figure 1:
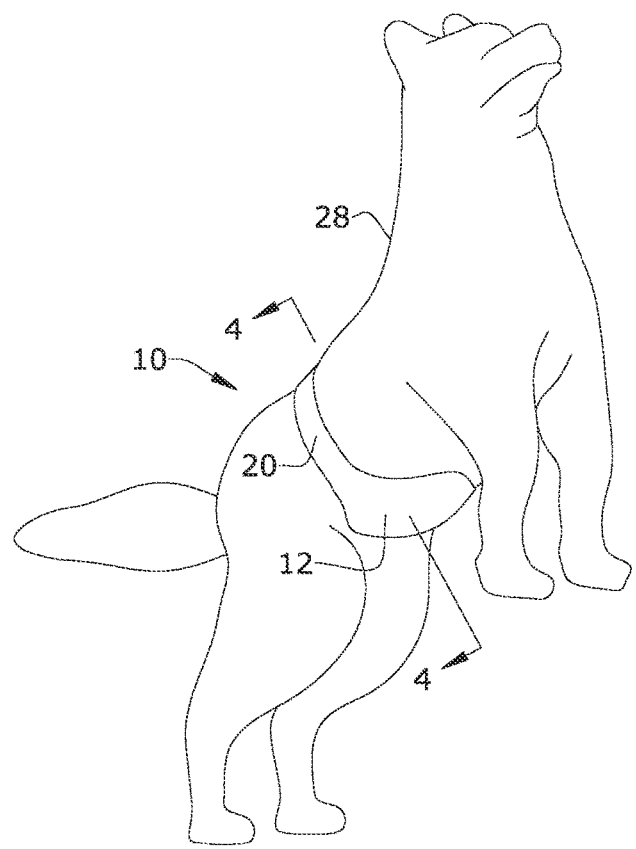
FIG. 1 is a perspective view of an embodiment of the present invention, shown in-use with a dog.

Referring now to FIGS. 1-5, a slim-profile belly band 10 with a buckle closure that goes around a waist/midsection of a dog 28 is disclosed. In certain embodiments, the band 10 may be provided with an outer layer 12, an inner layer 14, and a urine catching lining 16 attached to the inner layer 14 proximal where the genitals/belly area of the dog 28 is. These layers 12, 14 and lining 16 may be made from, for example, various appropriate fabrics, such as cotton, fleece, flannel, etc. The design of the band 10 is such that it is wide enough to cover the belly and genitals of the dog 28 and tapers to a thinner width (width being understood to be oriented in a direction perpendicular to the overall length of the band 10, i.e., the direction into the page in FIG. 4) as it goes up the side of the belly and around the back of the dog 28, as shown in FIG. 1. The lining 16 may be embodied as a soft, protective flannel lining 16 sewn to the inner layer 14 with stitching 26. In certain embodiments, the inner layer 14 and outer layer 12 may be provided as a single layer.

Figure 2:
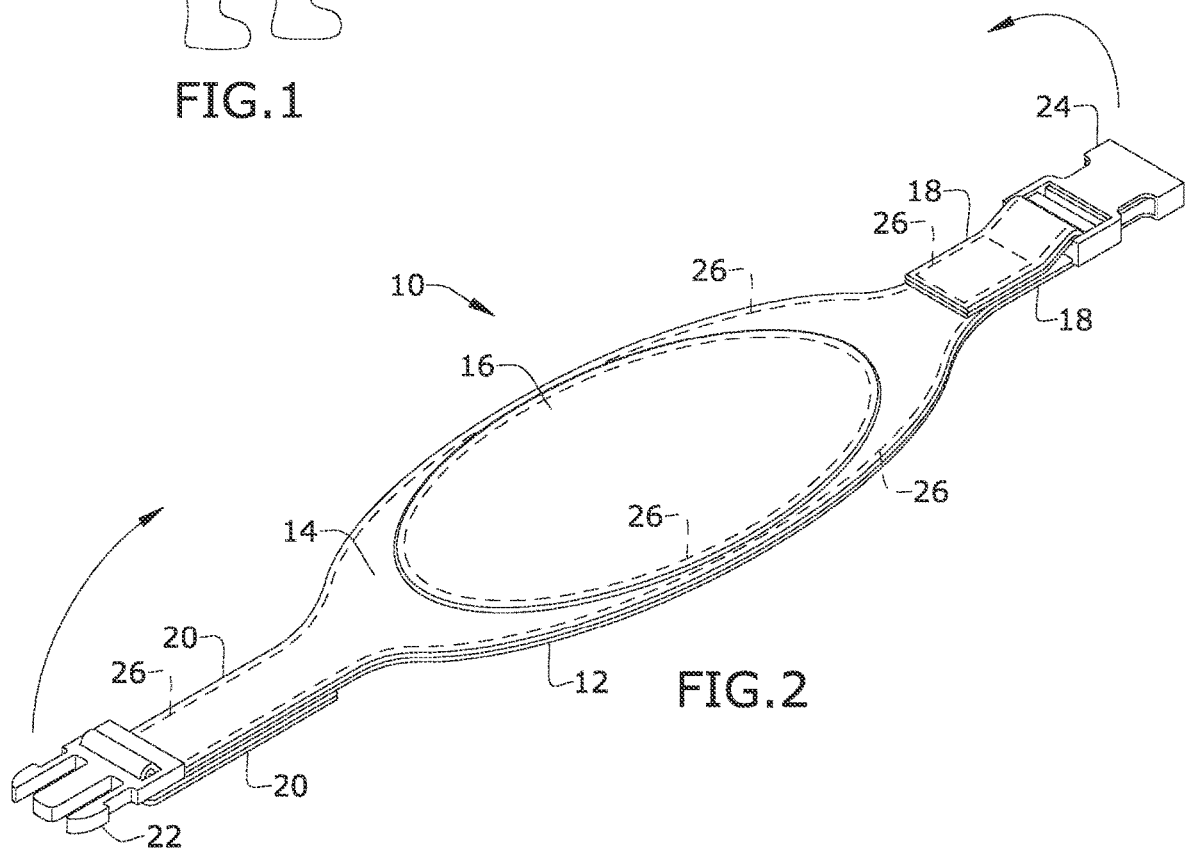
FIG. 2 is a perspective view of the embodiment of the present invention.
Figure 3:
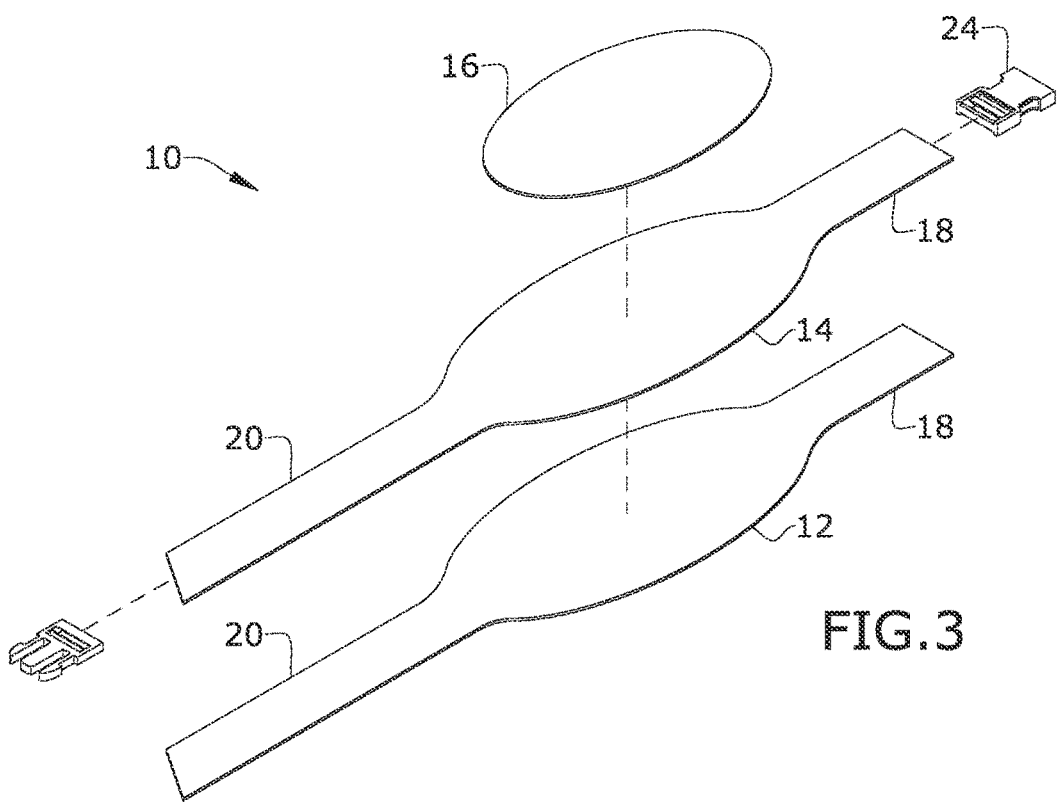
FIG. 3 is an exploded view of the embodiment of the present invention.
Figure 4:
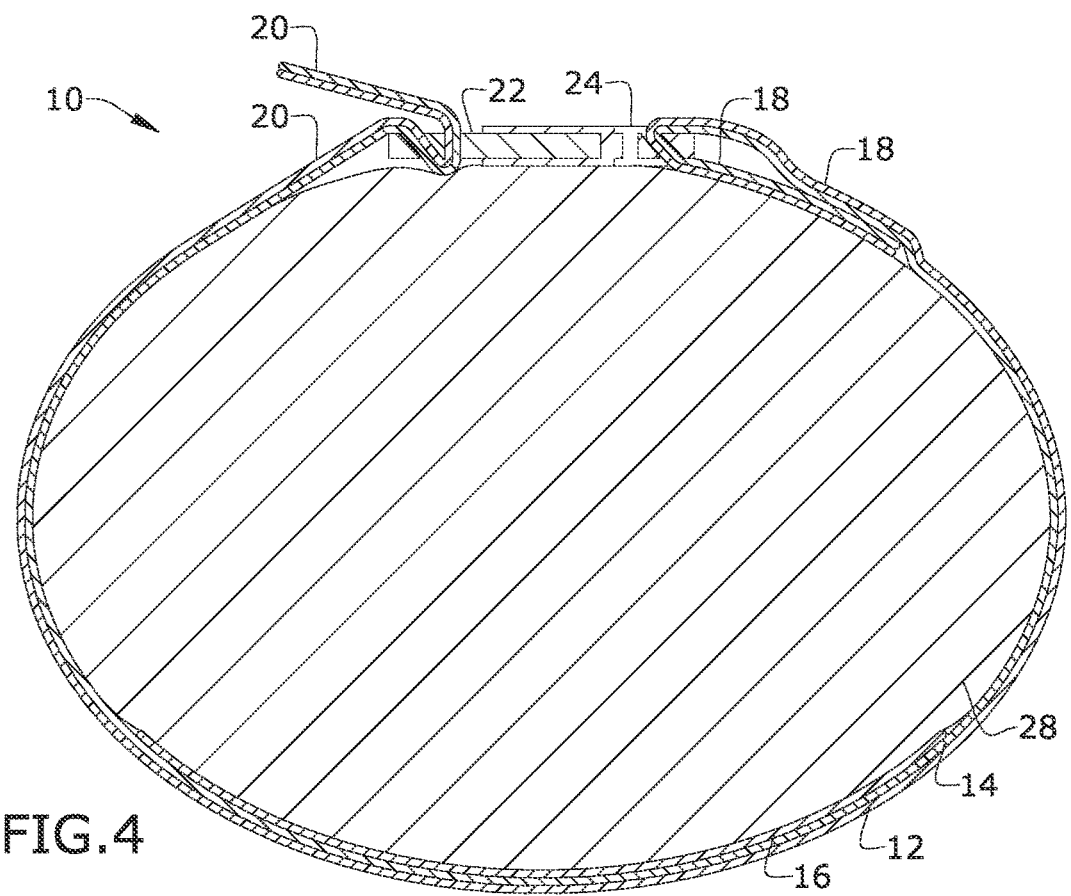
FIG. 4 is a cross-sectional view taken along line 4-4 of FIG. 1.
Figure 5:
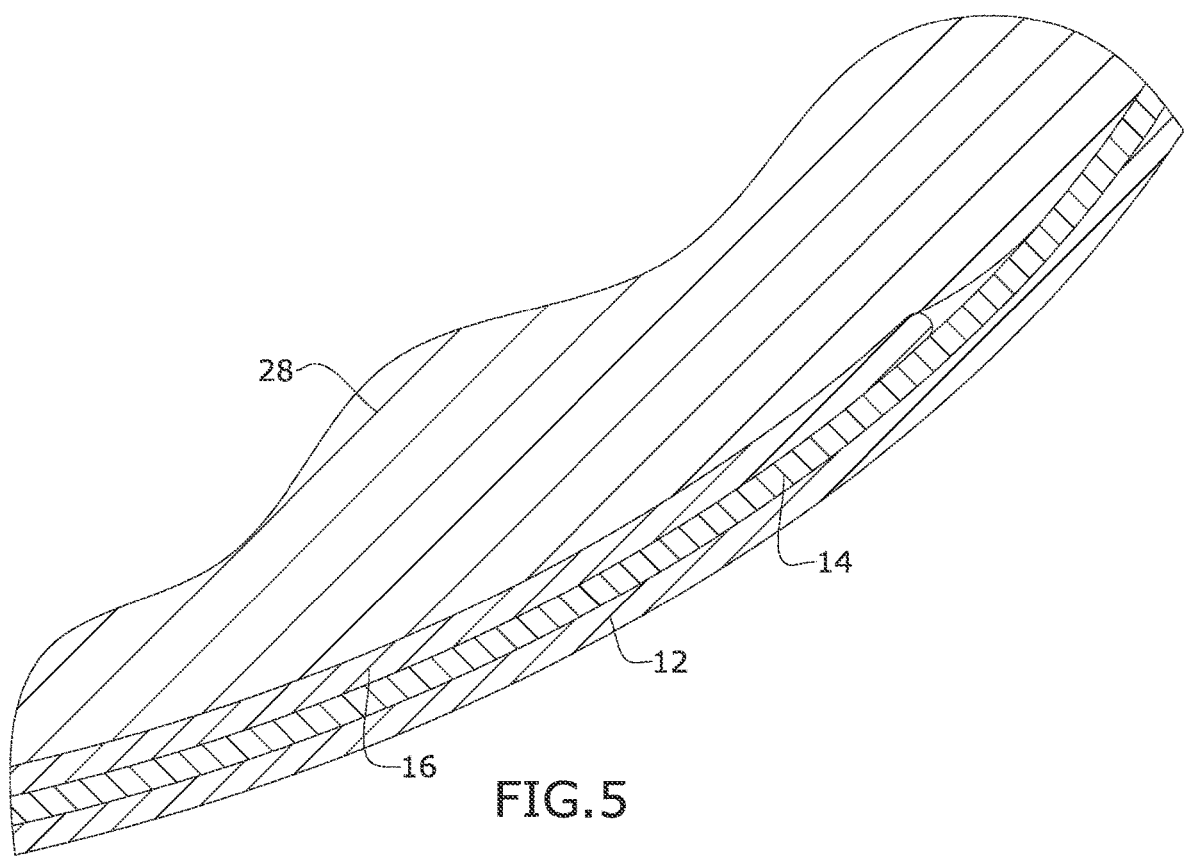
FIG. 5 is an enlarged detail view of a portion of FIG. 4.

As shown in FIGS. 2 and 3, the tapering referenced previously occurs between a mid-section/central portion of the band 10 (which resembles, at least partially, an oval-shape) and buckle straps 18, 20, which have a substantially thinner width than the mid-section. For example, the width of the buckle straps 18, 20 may be less than half, or even less than a third, of the width of the mid-section at its widest point. The wider central portion, in use, catches urine to prevent dogs 28 that are not yet potty trained from urinating on floor. It also protects against various scenarios as well, such as dogs 28 who may be marking a user's home or the homes of family or friends, or a dog that has bladder issues, like urine leakage.

Referring now to FIG. 2, a non-adjustable buckle strap 18 is provided on one side of the mid-section while an adjustable buckle strap 20 is provided on the other side of the mid-section. As also shown in FIG. 2, a female buckle 24 is attached to the non-adjustable buckle strap 18 and a male buckle 22 is attached to the adjustable buckle strap 20, but the male and female buckle portions are interchangeable in accordance with the present invention. In certain embodiments, the buckles 22, 24 may be sewn to the buckle straps 18, 20. Because of the thin, buckle straps 18, 20 utilized where the mating buckles 22, 24 are, there is less material on the dog's back and thus is more comfortable to wear.

As mentioned, due to the slim-profile design at buckle strap portions 18, 20 of the band 10, the band 10 is more comfortable to wear for the dog than conventional ones. Additionally, the buckle (constituted by the male buckle 22 and female buckle 24) doesn't make a noise when it is fastened and unfastened, so it does not frighten dogs who are afraid of loud noises. Dogs 28 cannot remove the band 10 because they cannot operate the buckle, and it is easier for a user to operate than hook and loop fasteners. In accordance with the present invention, the shape of band 10 could be re-configured by making it thicker or thinner at the central portion 40.

While the above disclosure makes clear various ways in that embodiments of the present invention may be made, a further method of making the present invention may include the following. A template of the belly band 10 may be provided in five sizes: extra-small, small, regular, large, and extra-large. Fabric is cut using one of the templates. The belly band 10 may be embodied as one continuous piece of fabric, with two of same size pieces of fabric (e.g., inner layer 14 and outer layer 12) being sewn together, with a protective liner 16 being sewn onto the fabric to cover the belly/genitals of a dog 28. The belly band 10 is provided with an adjustable strap 20 on one end that a male buckle 22 is sewn onto and a non-adjustable strap 18 that a female buckle 24 is sewn onto.

A method of using the present invention may include the following. A waist size of a dog 28 is measured, and the correct belly band size is selected. An incontinence pad may be inserted in the widest part of the belly band. The band is then put around the dog's waist, with the widest section covering dog's belly and genitals. Next, the two ends of the band 10 with the buckles 22, 24 are secured over the dog's back, and the adjustable buckle strap 20 is pull to a snug fit.

It will be appreciated that the figures, as illustrated, are not necessarily shown to scale or proportional, and are for illustrative purposes only. It should be understood, of course, that the foregoing relates to exemplary embodiments of the invention and that modifications may be made without departing from the spirit and scope of the invention as set forth in the following claims.

In the following claims, any labelling of elements, limitations, steps, or other parts of a claim (for example, first, second, etc., (a), (b), (c), etc., or (i), (ii), (iii), etc.) is only for purposes of clarity, and are not to be interpreted as suggesting any sort of ordering or precedence of the claim parts so labelled. If any such ordering or precedence is intended, it will be explicitly recited in the claim or, in some instances, it will be implicit or inherent based on the specific content of the claim. To further aid the USPTO and any readers of any patent issued on this application, it is additionally noted that there is no intent any of the appended claims to invoke paragraph (f) of 35 U.S.C. § 112 as it exists on the date of filing hereof unless the words "means for" or "step for" are explicitly used in the particular claim.

What is claimed is:

1. A band for attachment to a midsection of an animal, the band comprising:
   a central portion comprising a protective liner and having a first central portion width;
   a first buckle strap integral with and disposed on a first side of the central portion, the first buckle strap tapering in width from a first buckle strap width, proximal the central portion, to a second buckle strap width smaller that is smaller than the first buckle strap width, with the first buckle strap width having a smaller width that the first central portion width;
   a second buckle strap integral with and disposed on a second side of the central portion opposite the first side, the first buckle strap tapering in width from a third buckle strap width, proximal the central portion, to a fourth buckle strap width smaller that is smaller than the third buckle strap width, with the third buckle strap width having a smaller width that the first central portion width; and a buckle comprising a male buckle secured to a distal end of the first buckle strap and a female buckle secured to a distal end of the second buckle strap, the buckle being configured to latch over a back of the animal, and the protective liner being configured to cover an underside of the animal, wherein the central portion has a second central portion width, with the first central portion width corresponding to a width of the central portion at a centermost portion, and the second central portion width corresponding to a width of the central portion at distal ends of the central portion, the second central portion width being smaller than the first central portion width.

2. The band of claim 1, wherein the tapering in width of the first buckle strap and the second buckle strap occurs proximal to the central portion such that a remainder length of each of the first buckle strap and the second buckle strap has a substantially uniform width.

3. The band of claim 1, wherein the central portion defines a substantially oval shape, with the first central portion width being a widest dimension of the central portion.

4. The band of claim 1, wherein the second buckle strap width and the fourth buckle strap width are less than half of the first central portion width.

5. The band of claim 1, wherein the second buckle strap width and the fourth buckle strap width are less than a third of the first central portion width.

6. The band of claim 1, wherein one of the first buckle strap and the second buckle strap is adjustable in length.

7. The band of claim 1, wherein the central portion, the first buckle strap, and the second buckle strap are formed from an inner fabric layer joined to an outer fabric layer, with the protective liner being joined to the inner fabric layer.

8. The band of claim 1, wherein the central portion, the first buckle strap, and the second buckle strap comprise cotton, fleece, or flannel.

9. A band for attachment to a midsection of an animal, the band comprising:
    a central portion comprising a protective liner and having a first central portion width;
    a first buckle strap integral with and disposed on a first side of the central portion, the first buckle strap tapering in width from a first buckle strap width, proximal the central portion, to a second buckle strap width smaller that is smaller than the first buckle strap width, with the first buckle strap width having a smaller width that the first central portion width;
    a second buckle strap integral with and disposed on a second side of the central portion opposite the first side, the first buckle strap tapering in width from a third buckle strap width, proximal the central portion, to a fourth buckle strap width smaller that is smaller than the third buckle strap width, with the third buckle strap width having a smaller width that the first central portion width; and
    a buckle comprising a male buckle secured to a distal end of the first buckle strap and a female buckle secured to a distal end of the second buckle strap, the buckle being configured to latch over a back of the animal, and the protective liner being configured to cover an underside of the animal,
    wherein the central portion, the first buckle strap, and the second buckle strap are formed from an inner fabric layer joined to an outer fabric layer, with the protective liner being joined to the inner fabric layer.

10. The band of claim 9, wherein the tapering in width of the first buckle strap and the second buckle strap occurs proximal to the central portion such that a remainder length of each of the first buckle strap and the second buckle strap has a substantially uniform width.

11. The band of claim 9, wherein the central portion defines a substantially oval shape, with the first central portion width being a widest dimension of the central portion.

12. The band of claim 9, wherein the second buckle strap width and the fourth buckle strap width are less than half of the first central portion width.

13. The band of claim 9, wherein the second buckle strap width and the fourth buckle strap width are less than a third of the first central portion width.

14. The band of claim 9, wherein one of the first buckle strap and the second buckle strap is adjustable in length.

15. The band of claim 9, wherein the central portion, the first buckle strap, and the second buckle strap comprise cotton, fleece, or flannel.

* * * * *